(12) United States Patent
Marchiarullo et al.

(10) Patent No.: US 9,597,028 B2
(45) Date of Patent: Mar. 21, 2017

(54) BIOLOGICAL FLUID COLLECTION DEVICE AND BIOLOGICAL FLUID SEPARATION AND TESTING SYSTEM

(71) Applicant: Becton, Dickinson and Company, Franklin Lakes, NJ (US)

(72) Inventors: Daniel J. Marchiarullo, Morris Plains, NJ (US); Ashley Rachel Rothenberg, Morris Plains, NJ (US); Bradley M. Wilkinson, North Haledon, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 14/251,705

(22) Filed: Apr. 14, 2014

(65) Prior Publication Data

US 2014/0308165 A1 Oct. 16, 2014

Related U.S. Application Data

(60) Provisional application No. 61/811,918, filed on Apr. 15, 2013.

(51) Int. Cl.
*A61B 5/15* (2006.01)
*G01N 33/49* (2006.01)
(Continued)

(52) U.S. Cl.
CPC ...... *A61B 5/150213* (2013.01); *A61B 5/1411* (2013.01); *A61B 5/151* (2013.01);
(Continued)

(58) Field of Classification Search
CPC ........ A61B 5/150213; A61B 5/150412; A61B 5/150343; A61B 5/150778;
(Continued)

(56) References Cited

U.S. PATENT DOCUMENTS 3,322,114 A 5/1967 Portnoy et al.
3,640,393 A 2/1972 Hurtig
(Continued)

FOREIGN PATENT DOCUMENTS

| CN | 1382966 A | 12/2002 |
|---|---|---|
| CN | 101102847 A | 1/2008 |

(Continued)

OTHER PUBLICATIONS

Membrane Separation Technology for Research and Quality Control, Sartorius AG, Separation Technology, Laboratory Filtration; Mar. 1, 1997.

*Primary Examiner* — Lore Jarrett
(74) *Attorney, Agent, or Firm* — The Webb Law Firm

(57) ABSTRACT

A biological fluid collection device that is adapted to receive a multi-component blood sample having a cellular portion and a plasma portion is disclosed. After collecting the blood sample, the biological fluid collection device is able to separate the plasma portion from the cellular portion. After separation, the biological fluid collection device is able to transfer the plasma portion of the blood sample to a point-of-care testing device. The biological fluid collection device also provides a closed sampling and transfer system that reduces the exposure of a blood sample and provides fast mixing of a blood sample with an anticoagulant. The biological fluid collection device is engageable with a testing device for closed transfer of a portion of the plasma portion from the biological fluid collection device to the testing device. The testing device is adapted to receive the plasma portion to analyze the blood sample and obtain test results.

27 Claims, 9 Drawing Sheets

(51) Int. Cl.
  *A61M 1/34* (2006.01)
  *G01N 1/28* (2006.01)
  *G01N 1/40* (2006.01)
  *G01N 1/34* (2006.01)
  *B01L 3/00* (2006.01)
  *B04B 7/08* (2006.01)
  *A61B 5/151* (2006.01)
  *A61B 5/157* (2006.01)

(52) U.S. Cl.
  CPC ........ *A61B 5/157* (2013.01); *A61B 5/150022* (2013.01); *A61B 5/15101* (2013.01); *A61B 5/15105* (2013.01); *A61B 5/15144* (2013.01); *A61B 5/15198* (2013.01); *A61B 5/150221* (2013.01); *A61B 5/150267* (2013.01); *A61B 5/150305* (2013.01); *A61B 5/150343* (2013.01); *A61B 5/150351* (2013.01); *A61B 5/150412* (2013.01); *A61B 5/150748* (2013.01); *A61B 5/150755* (2013.01); *A61B 5/150778* (2013.01); *A61M 1/34* (2013.01); *B01L 3/502* (2013.01); *B01L 3/5021* (2013.01); *B04B 7/08* (2013.01); *G01N 1/28* (2013.01); *G01N 1/34* (2013.01); *G01N 1/4005* (2013.01); *G01N 1/4077* (2013.01); *G01N 33/491* (2013.01); *A61B 5/150435* (2013.01); *A61B 5/150442* (2013.01); *A61B 5/150969* (2013.01); *B01L 2200/0631* (2013.01); *B01L 2200/10* (2013.01); *B01L 2300/0681* (2013.01); *B01L 2400/0478* (2013.01); *G01N 2001/4016* (2013.01); *G01N 2001/4088* (2013.01)

(58) Field of Classification Search
  CPC ........ A61B 5/150755; A61B 5/150748; A61B 5/151; A61B 5/15198; A61B 5/15105; A61B 5/150022; B01L 3/5021; B01L 3/502; B04B 7/08
  See application file for complete search history.

(56) References Cited

U.S. PATENT DOCUMENTS

| | | | |
|---|---|---|---|
| 4,511,349 | A | 4/1985 | Nielsen et al. |
| 4,627,445 | A | 12/1986 | Garcia et al. |
| 5,055,203 | A | 10/1991 | Columbus |
| 5,163,442 | A | 11/1992 | Ono |
| 5,219,999 | A | 6/1993 | Suzuki et al. |
| 5,422,018 | A | 6/1995 | Saunders et al. |
| 5,636,640 | A | 6/1997 | Staehlin |
| 5,726,026 | A | 3/1998 | Wilding et al. |
| 5,839,715 | A | 11/1998 | Leinsing |
| 5,922,591 | A * | 7/1999 | Anderson et al. ......... 435/287.2 |
| 6,074,183 | A | 6/2000 | Allen et al. |
| 6,264,619 | B1 | 7/2001 | Ferguson |
| 6,506,167 | B1 | 1/2003 | Ishimito et al. |
| 6,869,405 | B2 | 3/2005 | Marsden |
| 8,158,410 | B2 | 4/2012 | Tang et al. |
| 2002/0009015 | A1 * | 1/2002 | Laugharn et al. ............ 366/108 |
| 2002/0143298 | A1 | 10/2002 | Marsden |
| 2003/0134416 | A1 | 7/2003 | Yamanishi et al. |
| 2004/0142463 | A1 | 7/2004 | Walker et al. |
| 2004/0143226 | A1 | 7/2004 | Marsden |
| 2004/0230216 | A1 | 11/2004 | Levaughn et al. |
| 2005/0069459 | A1 | 3/2005 | Ahn et al. |
| 2005/0214927 | A1 * | 9/2005 | Haley ....................... 435/283.1 |
| 2006/0029923 | A1 | 2/2006 | Togawa et al. |
| 2006/0240964 | A1 | 10/2006 | Lolachi et al. |
| 2007/0031283 | A1 | 2/2007 | Davis et al. |
| 2007/0160503 | A1 | 7/2007 | Sethu et al. |
| 2008/0135502 | A1 | 6/2008 | Pyo et al. |
| 2008/0240990 | A1 | 10/2008 | Flaherty |
| 2009/0004060 | A1 | 1/2009 | Omuro et al. |
| 2009/0136982 | A1 | 5/2009 | Tang et al. |
| 2009/0181411 | A1 | 7/2009 | Battrell et al. |
| 2009/0204026 | A1 | 8/2009 | Crawford et al. |
| 2010/0089815 | A1 | 4/2010 | Zhang et al. |
| 2010/0093551 | A1 | 4/2010 | Montagu |
| 2010/0198108 | A1 | 8/2010 | Alden |
| 2010/0241031 | A1 | 9/2010 | Lai |
| 2011/0124130 | A1 | 5/2011 | Wagner et al. |
| 2011/0124984 | A1 | 5/2011 | Rostaing |
| 2012/0152858 | A1 | 6/2012 | Yang |
| 2012/0275955 | A1 | 11/2012 | Haghgooie et al. |
| 2012/0277696 | A1 | 11/2012 | Gonzalez-Zugasti et al. |
| 2012/0277697 | A1 | 11/2012 | Haghgooie et al. |
| 2013/0026085 | A1 * | 1/2013 | Samsoondar ................. 210/136 |
| 2013/0052675 | A1 | 2/2013 | Karlsson et al. |
| 2013/0082012 | A1 | 4/2013 | Lean et al. |
| 2013/0086980 | A1 | 4/2013 | Gadini et al. |
| 2013/0175213 | A1 | 7/2013 | Dorrer et al. |
| 2013/0209331 | A1 | 8/2013 | Rodenfels et al. |

FOREIGN PATENT DOCUMENTS

| | | |
|---|---|---|
| CN | 101332320 A | 12/2008 |
| CN | 102764133 A | 11/2012 |
| DE | 202008010918 U1 | 1/2009 |
| EP | 0376168 A2 | 7/1990 |
| EP | 0747105 A2 | 12/1996 |
| EP | 1096254 A2 | 5/2001 |
| EP | 1106065 A2 | 6/2001 |
| EP | 1477804 A1 | 11/2004 |
| EP | 1602329 A1 | 12/2005 |
| EP | 1627651 A2 | 2/2006 |
| EP | 2264453 A1 | 12/2010 |
| EP | 2413138 A2 | 2/2012 |
| FR | 2929135 A1 | 10/2009 |
| FR | 2977808 A1 | 1/2013 |
| JP | 2004361419 A | 12/2004 |
| WO | 9309710 A1 | 5/1993 |
| WO | 2005018710 A2 | 3/2005 |
| WO | 2006047831 A1 | 5/2006 |
| WO | 2007002579 A2 | 1/2007 |
| WO | 2009123592 A1 | 10/2009 |
| WO | 2011040874 A1 | 4/2011 |
| WO | 2012121686 A1 | 9/2012 |

* cited by examiner

BIOLOGICAL FLUID COLLECTION DEVICE AND BIOLOGICAL FLUID SEPARATION AND TESTING SYSTEM

CROSS REFERENCE TO RELATED APPLICATIONS

The present application claims priority to U.S. Provisional Application No. 61/811,918, filed Apr. 15, 2013, entitled "Medical Device for Collection of a Biological Sample", the entire disclosure of which is hereby incorporated by reference in its entirety.

BACKGROUND OF THE INVENTION

1. Field of the Disclosure

The present disclosure relates generally to devices, assemblies, and systems adapted for use with vascular access devices. More particularly, the present disclosure relates to devices, assemblies, and systems adapted for collecting biological samples for use in point-of-care testing.

2. Description of the Related Art

Blood sampling is a common health care procedure involving the withdrawal of at least a drop of blood from a patient. Blood samples are commonly taken from hospitalized, homecare, and emergency room patients either by finger stick, heel stick, or venipuncture. Once collected, blood samples may be analyzed to obtain medically useful information including chemical composition, hematology, or coagulation, for example.

Blood tests determine the physiological and biochemical states of the patient, such as disease, mineral content, drug effectiveness, and organ function. Blood tests may be performed in a clinical laboratory or at the point-of-care near the patient. One example of point-of-care blood testing is the routine testing of a patient's blood glucose levels which involves the extraction of blood via a finger stick and the mechanical collection of blood into a diagnostic cartridge. Thereafter, the diagnostic cartridge analyzes the blood sample and provides the clinician a reading of the patient's blood glucose level. Other devices are available which analyze blood gas electrolyte levels, lithium levels, and ionized calcium levels. Some other point-of-care devices identify markers for acute coronary syndrome (ACS) and deep vein thrombosis/pulmonary embolism (DVT/PE).

Despite the rapid advancement in point-of-care testing and diagnostics, blood sampling techniques have remained relatively unchanged. Blood samples are frequently drawn using hypodermic needles or vacuum tubes attached to a proximal end of a needle or a catheter assembly. In some instances, clinicians collect blood from a catheter assembly using a needle and syringe that is inserted into the catheter to withdraw blood from a patient through the inserted catheter. These procedures utilize needles and vacuum tubes as intermediate devices from which the collected blood sample is typically withdrawn prior to testing. These processes are thus device intensive, utilizing multiple devices in the process of obtaining, preparing, and testing blood samples. Each additional device increases the time and cost of the testing process.

Point-of-care testing devices allow for a blood sample to be tested without needing to send the blood sample to a lab for analysis. Thus, it is desirable to create a device that provides an easy, safe, reproducible, and accurate process with a point-of-care testing system.

SUMMARY OF THE INVENTION

The present disclosure provides a biological fluid collection device, such as a blood collection device, that is adapted to receive a multi-component blood sample having a cellular portion and a plasma portion. After collecting the blood sample, the biological fluid collection device is able to separate the plasma portion from the cellular portion. After separation, the biological fluid collection device is able to transfer the plasma portion of the blood sample to a point-of-care testing device. The biological fluid collection device of the present disclosure also provides a closed sampling and transfer system that reduces the exposure of a blood sample and provides fast mixing of a blood sample with a sample stabilizer or preservative. The biological fluid collection device is engageable with a biological fluid testing device, such as a blood testing device, for closed transfer of a portion of the plasma portion from the biological fluid collection device to the biological fluid testing device. The biological fluid testing device is adapted to receive the plasma portion to analyze the blood sample and obtain test results.

Some of the advantages of the biological fluid collection device and the biological fluid separation and testing system of the present disclosure over prior systems are that it is a closed system which reduces blood sample exposure, it provides automatic and fast mixing of the blood sample with an anticoagulant, it facilitates separation of the blood sample without transferring the blood sample to a separate device, and it is capable of transferring pure plasma to a point-of-care testing device. The biological fluid collection device of the present disclosure enables integrated biological fluid collection and plasma creation in a closed system without centrifugation. The clinician may collect and separate the blood sample and then immediately transfer the plasma portion to the point-of-care testing device without further manipulation. This enables collection and transfer of plasma to the point-of-care testing device without exposure to blood. In addition, the biological fluid collection device of the present disclosure minimizes process time by processing the blood within the biological fluid collection device and without external machinery. Further, it eliminates the waste associated with blood collection and plasma separation for an evacuated tube for tests which only require small amounts of blood.

In accordance with an embodiment of the present invention, a biological fluid collection device for a multi-component blood sample includes a housing having an inlet port, an outlet port, a first flow channel defined within the housing and in fluid communication with the inlet port, and a second flow channel defined within the housing and in fluid communication with the outlet port. The device also includes a valve disposed between the first flow channel and the second flow channel which is transitionable between a closed position and an open position. When the valve is in the closed position, the first flow channel is in fluid isolation from the second flow channel, and when the valve is in the open position, the first flow channel is in fluid communication with the second flow channel. The second flow channel includes a collection chamber having a separation member disposed therein and a blood component chamber defined therein in communication with the separation member.

In certain configurations, the inlet port is adapted to receive the multi-component blood sample. The multi-component blood sample may include a cellular portion and a plasma portion. The separation member is adapted to allow the plasma portion to pass through the separation member and into the blood component chamber. The separation member may be a lateral flow filter. The device may also include an actuation member in communication with the inlet port which is transitionable from an initial position in which a portion of the actuation member is disposed within the housing in an initial position, to an activated position in which the same portion of the actuation member is displaced from the initial position within the housing and the multi-component blood sample is drawn into the first flow channel of the housing through the inlet port.

In other configurations, the actuation member includes a plunger. The device may also include a drive element in communication with the inlet port, the drive element may be adapted to assist the flow of the multi-component blood sample within the inlet port. The drive element may include an acoustic driver. In certain configurations, the first flow channel may include a sample stabilizer. The first flow channel may also include at least one agitation member. Optionally, the first flow channel may include at least one agitation flute co-molded therein and the at least one agitation flute may have at least one sample stabilizer coated thereon.

The first flow channel may include a sample stabilizer, and the inlet port may be adapted to receive the multi-component blood sample, and the valve may be transitionable from the closed position to the open position subsequent to mixing of the multi-component blood sample within the first flow channel. The outlet port may be in communication with the blood component chamber. The inlet port may be adapted to receive the multi-component blood sample having a cellular portion and a plasma portion. The outlet port may be adapted for connection to a point-of-care testing device for closed transfer of at least a portion of the plasma portion from the blood component chamber to the point-of-care testing device. In certain configurations, the device also includes a pressure regulator in fluid communication with at least one of the inlet port, the first flow channel, the valve, the second flow channel, the collection chamber, the blood component chamber, the separation member, and the outlet port. The valve may be a rotatable stop-cock.

In accordance with another embodiment of the present invention, a multi-component biological fluid sample separation and testing system, such as a blood sample separation and testing system, includes a biological fluid collection and separation device, such as a blood collection and separation device. The biological fluid collection and separation device may include a housing having an inlet port, an outlet port, a first flow channel defined within the housing and in fluid communication with the inlet port, and a second flow channel defined within the housing and in fluid communication with the outlet port. The inlet port may be configured to receive a multi-component blood sample. The device may also include a valve disposed between the first flow channel and the second flow channel which is transitionable between a closed position and an open position. When the valve is in the closed position, the first flow channel is in fluid isolation from the second flow channel, and when the valve is in the open position, the first flow channel is in fluid communication with the second flow channel. The second flow channel may include a collection chamber having a separation member disposed therein and the housing may further include a blood component chamber defined therein in communication with the separation member. The system may include a testing device having a receiving port adapted to receive the outlet port of the biological fluid collection and separation device for closed transfer of a portion of the multi-component blood sample from the blood component chamber to the testing device.

In certain configurations, the testing device is a point-of-care testing device. The multi-component blood sample received in the inlet port may include a cellular portion and a plasma portion. The separation member may be adapted to allow the plasma portion to pass through the separation member and into the blood component chamber. The separation member may be a lateral flow filter. The first flow channel may include at least one sample stabilizer. The first flow channel may also include at least one agitation member located therein.

BRIEF DESCRIPTION OF THE DRAWINGS

The above-mentioned and other features and advantages of this disclosure, and the manner of attaining them, will become more apparent and the disclosure itself will be better understood by reference to the following descriptions of embodiments of the disclosure taken in conjunction with the accompanying drawings, wherein.

Corresponding reference characters indicate corresponding parts throughout the several views. The exemplifications set out herein illustrate exemplary embodiments of the disclosure, and such exemplifications are not to be construed as limiting the scope of the disclosure in any manner.

DETAILED DESCRIPTION

Figure 1:
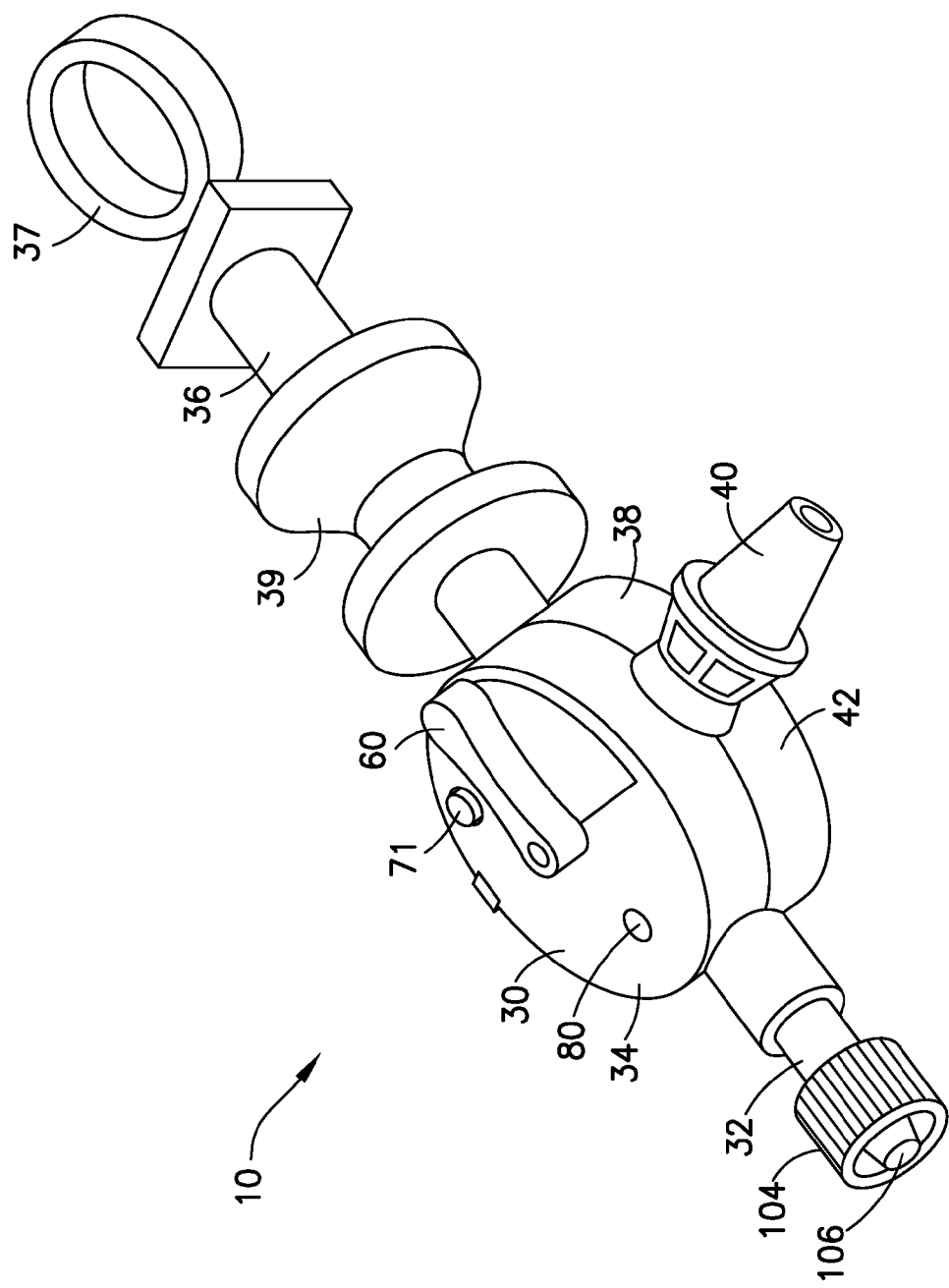
FIG. 1 is a perspective view of a biological fluid collection device in accordance with an embodiment of the present invention.

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume alternative variations and step sequences, except where expressly specified to the contrary. It is also to be understood that the specific devices and processes illustrated in the attached drawings, and described in the following specification, are simply exemplary embodiments of the invention. Hence, specific dimensions and other physical characteristics related to the embodiments disclosed herein are not to be considered as limiting.

Various point-of-care testing devices are known in the art. Such point-of-care testing devices include test strips, glass slides, diagnostic cartridges, or other testing devices for testing and analysis. Test strips, glass slides, and diagnostic cartridges are point-of-care testing devices that receive a blood sample and test that blood for one or more physiological and biochemical states. There are many point-of-care devices that use cartridge based architecture to analyze very small amounts of blood bedside without the need to send the sample to a lab for analysis. This saves time in getting results over the long run but creates a different set of challenges versus the highly routine lab environment. Examples of such testing cartridges include the i-STAT® testing cartridge from the Abbot group of companies. Testing cartridges such as the i-STAT® cartridges may be used to test for a variety of conditions including the presence of chemicals and electrolytes, hematology, blood gas concentrations, coagulation, or cardiac markers. The results of tests using such cartridges are quickly provided to the clinician.

However, the samples provided to such point-of-care testing cartridges are currently manually collected with an open system and transferred to the point-of-care testing cartridge in a manual manner that often leads to inconsistent results, thereby negating the advantage of the point-of-care testing device. Accordingly, a need exists for a system for collecting and transferring a sample to a point-of-care testing device that provides safer, reproducible, and more accurate results. Accordingly, a point-of-care collecting and transferring system of the present disclosure will be described hereinafter. A system of the present disclosure enhances the reliability of the point-of-care testing device by: 1) incorporating a more closed type of sampling and transfer system; 2) minimizing open exposure of the sample; 3) improving sample quality; 4) improving the overall ease of use; and 5) separating the sample at the point of collection.

Figure 2:
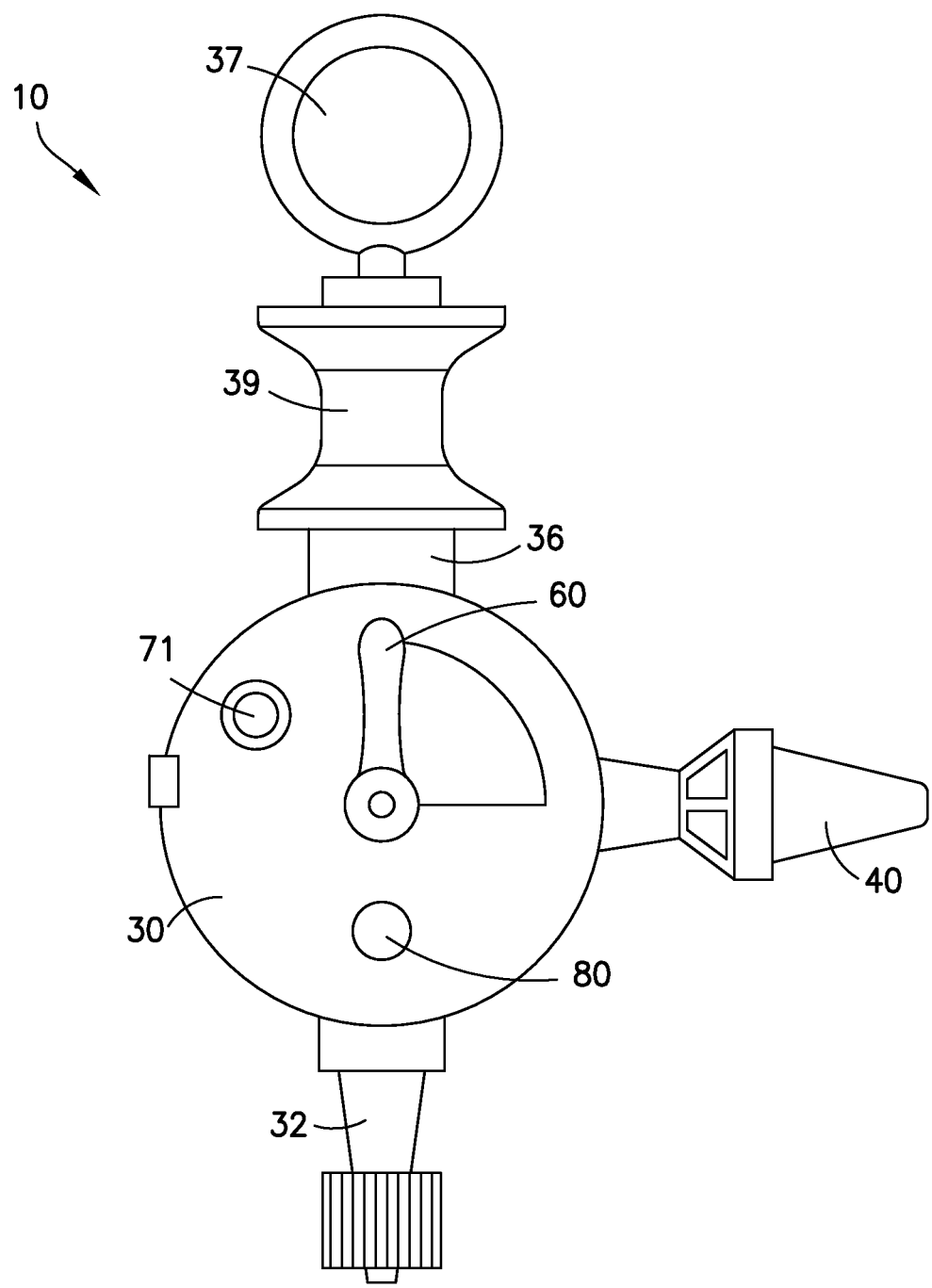
FIG. 2 is an elevation view of a biological fluid collection device in accordance with an embodiment of the present invention.
Figure 3:
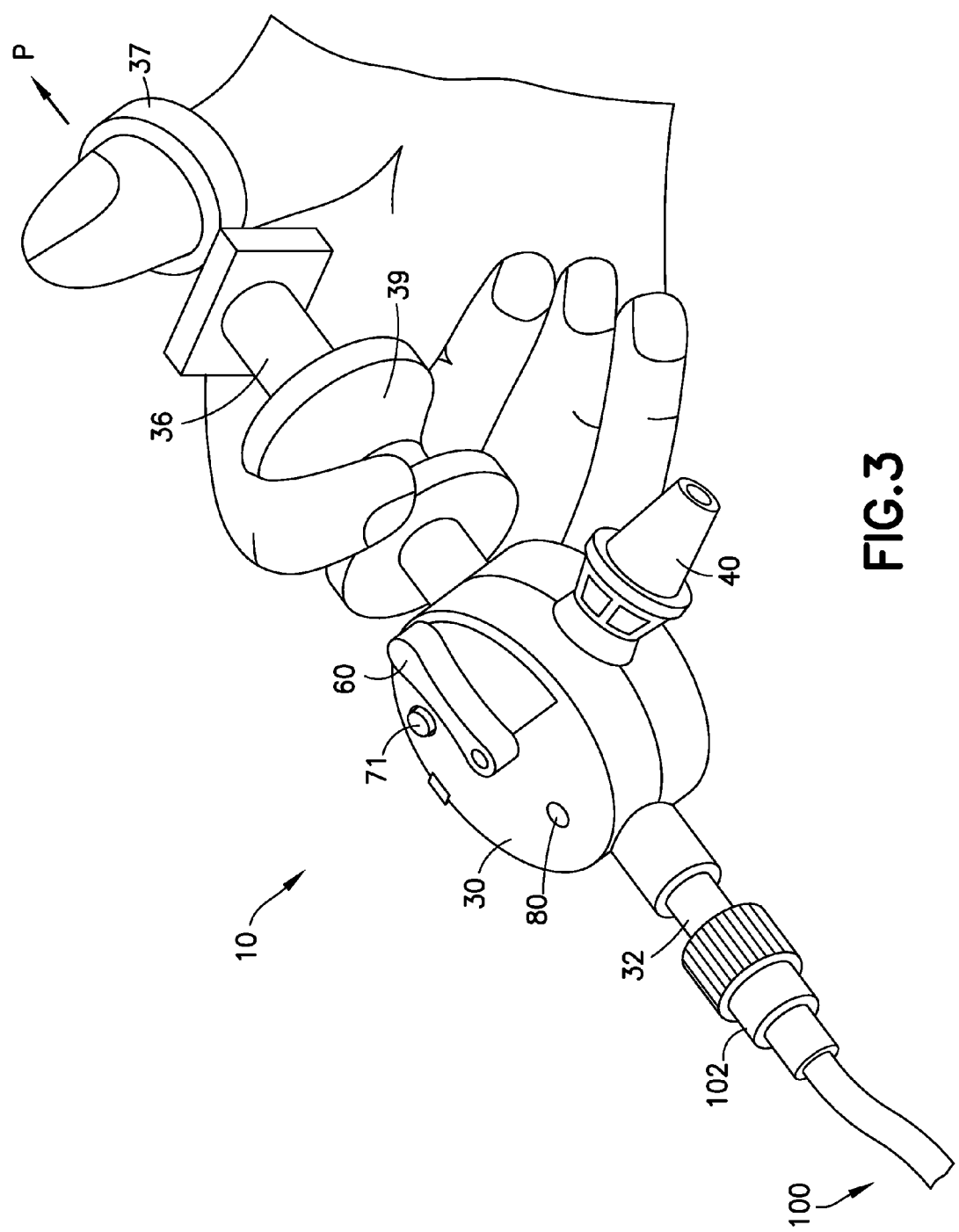
FIG. 3 is a perspective view of a biological fluid collection device in accordance with an embodiment of the present invention.
Figure 4:
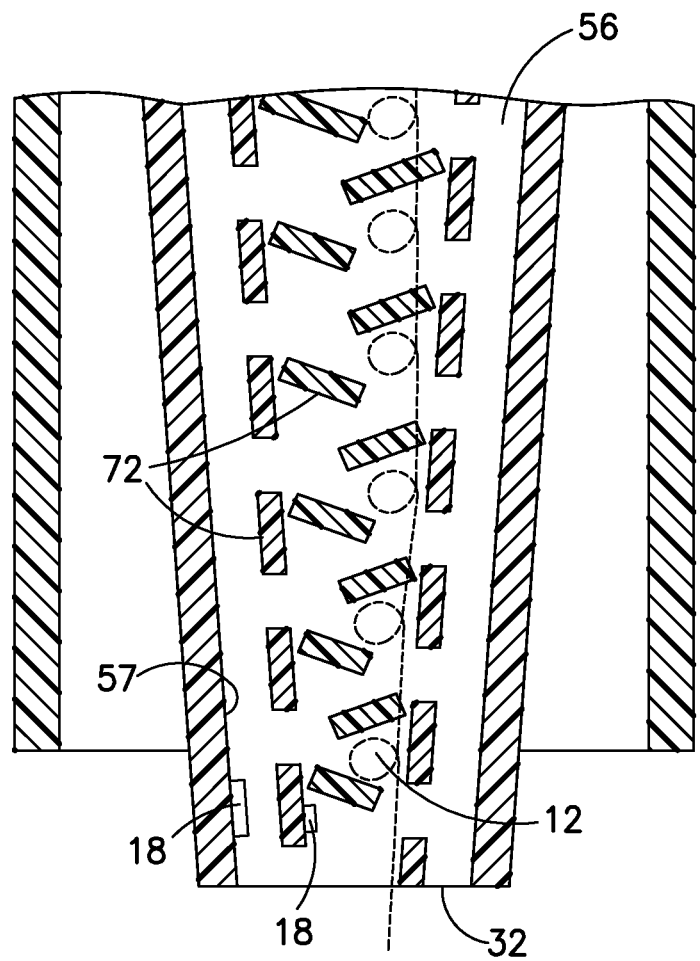
FIG. 4 is a schematic representation of an agitation member within an inlet port of a biological fluid collection device in accordance with an embodiment of the present invention.
Figure 5:
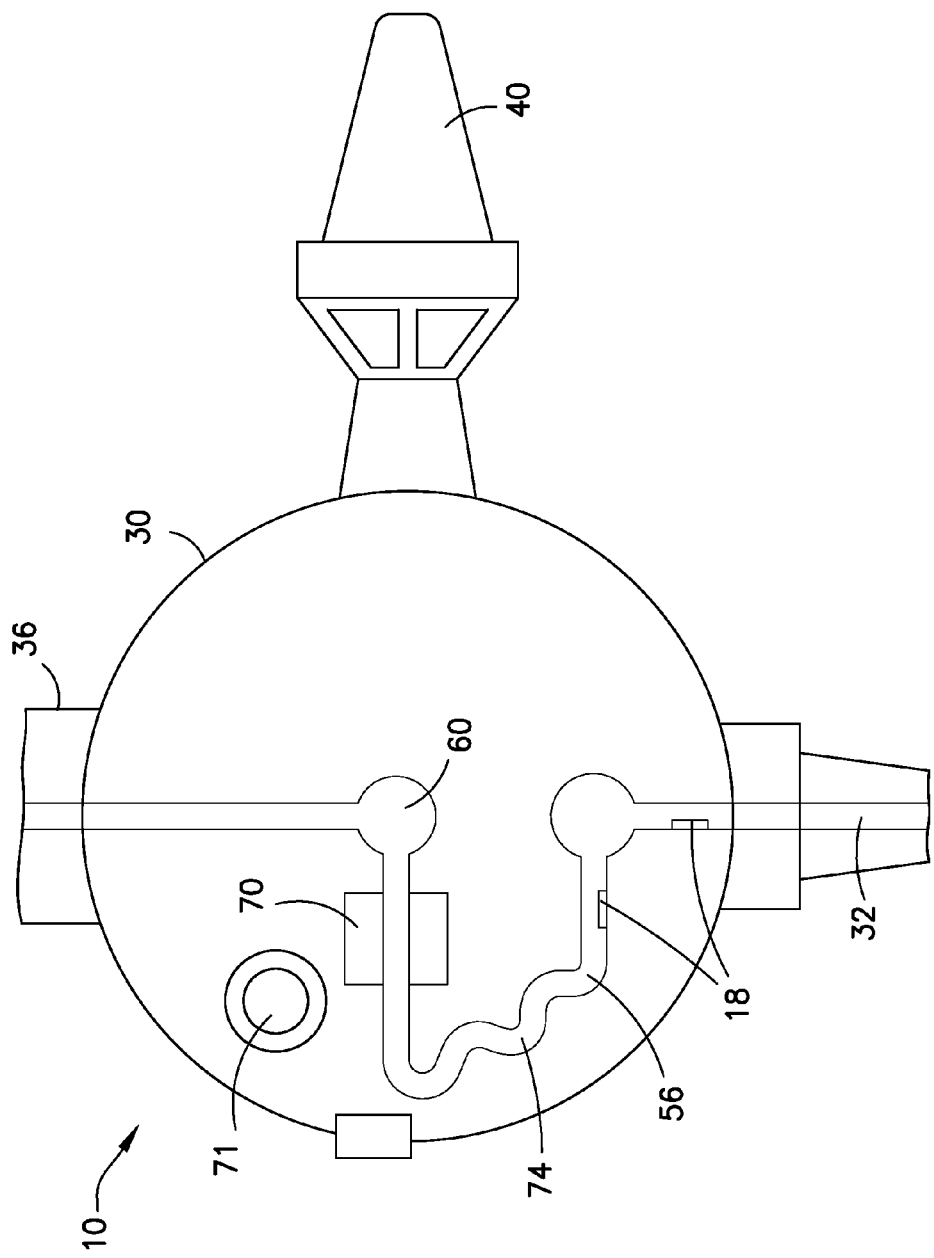
FIG. 5 is an elevation view of a biological fluid collection device in accordance with an embodiment of the present invention, with a valve in a closed position and illustrating a first flow channel.
Figure 6:
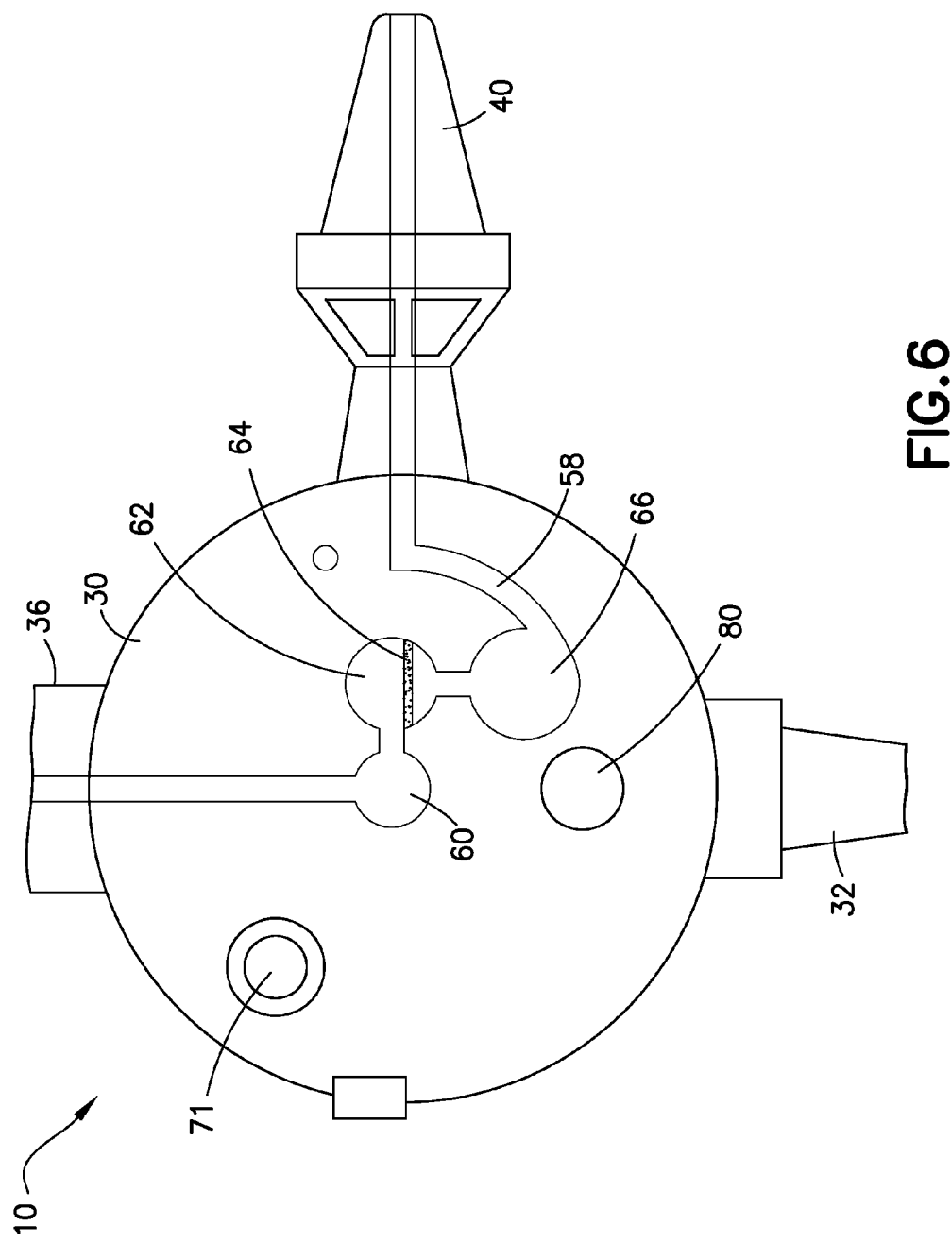
FIG. 6 is an elevation view of a biological fluid collection device in accordance with an embodiment of the present invention, with a valve in an open position and illustrating a second flow channel.
Figure 7:
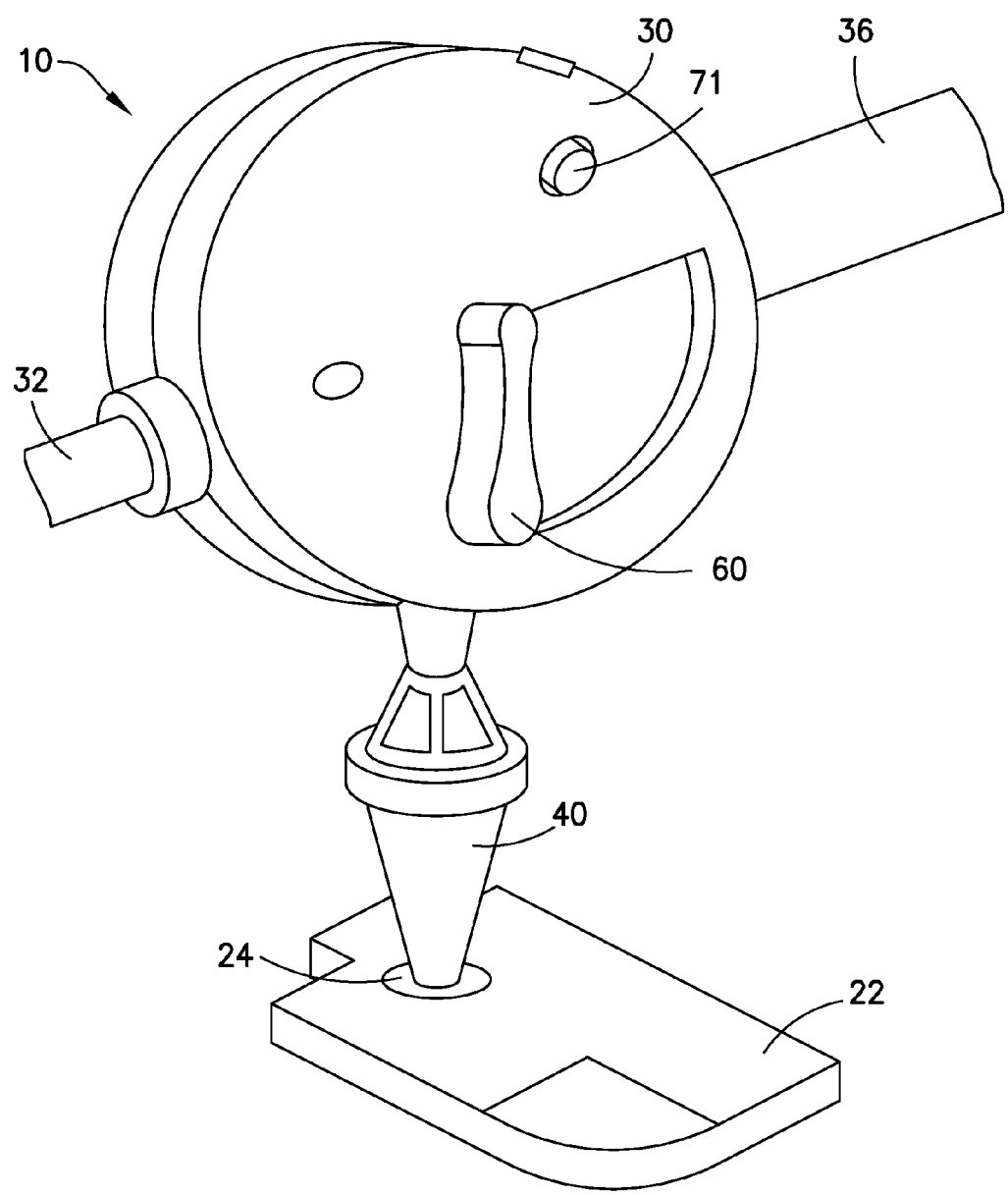
FIG. 7 is a perspective view of a biological fluid collection device and a point-of-care testing device in accordance with an embodiment of the present invention.
Figure 8:
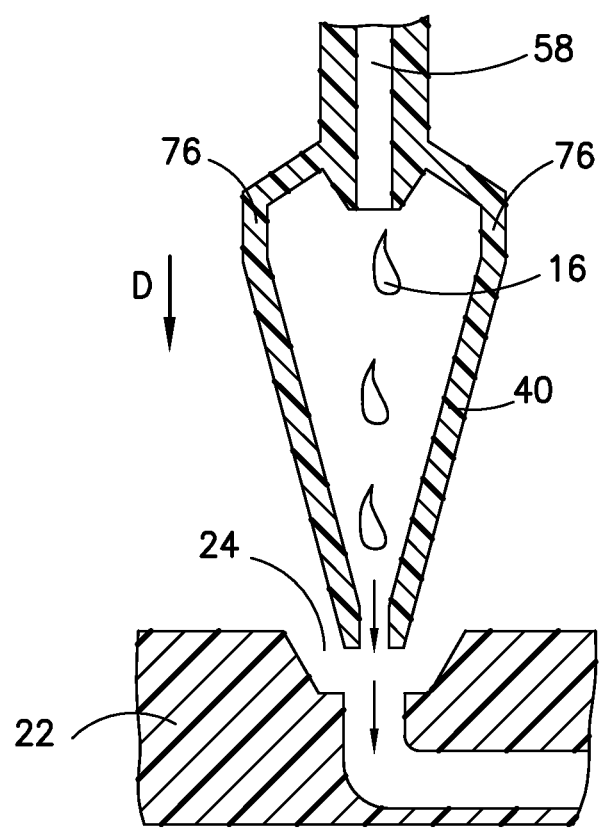
FIG. 8 is a cross-sectional view of a septum of a biological fluid collection device in accordance with an embodiment of the present invention.

Reference is now made to FIGS. 1-9 which illustrate a biological fluid or blood collection device, generally indicated as 10, in accordance with an embodiment of the present invention. The blood collection device 10 is configured to collect a multi-component blood sample, separate the sample, and supply a portion of the sample to a point-of-care testing device. In certain instances, the blood collection device 10 may be configured to stabilize a sample and transfer all or a portion of the stabilized sample to a test cartridge. Specifically, the blood collection device may be adapted to receive a multi-component blood sample 12 having a first portion, or cellular portion 14, and a second portion, or plasma portion 16. After collecting the blood sample 12, the blood collection device 10 is able to separate the plasma portion 16 from the cellular portion 14. After separation, the blood collection device 10 is able to transfer the plasma portion 16 of the blood sample 12 to a point-of-care testing device 22, as shown in FIGS. 7-8. The blood collection device 10 of the present disclosure also provides a closed separation system that reduces the exposure of the blood sample 12 and provides fast mixing of the blood sample 12 with at least one of a sample stabilizer or preservative 18, as illustrated in FIG. 4.

It can be appreciated that the sample stabilizer or preservative 18 can include any one or more of an anticoagulant or a substance, well known in the art that can be used to preserve a specific element within a blood sample, such as RNA, a protein analyte, and the like.

Referring in particular to FIGS. 1-3, there is shown the blood collection device 10 including a housing 30 having an inlet port 32 extending from a first end 34 of the housing 30. An actuation member, such as a plunger 36 extends from a second end 38 of the housing 30. It can be appreciated that the plunger 36 can have any shape or design known in the art. According to one embodiment, the plunger 36 can have an ergonomic design including a ring 37 and a grasping portion 39 that assists the clinician with manipulation of the device 10 and actuation of the plunger 36. According to one embodiment, the second end 38 of the housing 30 can be at a location that is opposite from the first end 34 of the housing 30. The housing 30 also includes an outlet port or dispenser 40, which can extend from a side portion 42 of the housing 30. The inlet port 32 is configured for connection to a blood collection set 100.

According to one embodiment, as shown in FIG. 3, the inlet port 32 is adapted to be connected to a blood collection set, generally indicated as 100, to allow for the collection of a multi-component blood sample 12 into the blood collection device 10. The inlet port 32 may be sized and adapted for engagement with the separate blood collection set 100, such as a needle assembly or IV connection assembly and, therefore, may include a mechanism for such engagement as is conventionally known. For example, in one embodiment, the inlet port 32 may include a luer lock or luer tip for engagement with an optional separate luer mating component of such a separate device for attachment therewith. For example, referring to FIGS. 1-3, the blood collection set 100 may include a luer component 102 for engagement with inlet port 32 of blood collection device 10. In this manner, the inlet port 32 is connectable to the blood collection set 100 for the collection of a blood sample into the blood collection device 10. In addition, a mechanism for locking engagement, such as a spin lock luer 104 having a male luer tip and activated port 106 between the inlet port 32 and the blood collection set 100 may also be provided. Such luer connections and luer locking mechanisms are well known in the art. The blood collection set 100 may include a needle assembly, an IV connection assembly, a PICC line, an arterial indwelling line, or similar blood collection means.

With continuing reference to FIGS. 1-3 and with reference to FIGS. 5-6, a first flow channel 56 is defined within the housing 30 and in fluid communication with the inlet port 32. A second flow channel 58 is defined within the housing 30 and in fluid communication with the outlet port 40. A valve 60 is disposed between the first flow channel 56 and the second flow channel 58. The valve is transitionable between a closed position and an open position, wherein with the valve 60 in the closed position, the first flow channel 56 is in fluid isolation from the second flow channel 58, and wherein with the valve 60 in the open position, the first flow channel 56 is in fluid communication with the second flow channel 58. According to one embodiment, the valve 60 can be a manually rotatable stop cock valve, however, it can be appreciated that the valve can be any known valve that is configured to transition between a closed position and an open position. As shown in FIG. 6, the second flow channel 58 includes a collection chamber 62 having a separation member, such as a filter 64. The second flow channel 58 also includes a blood component chamber, such as a plasma chamber 66 associated therewith and in communication with the filter 64.

Figure 9:
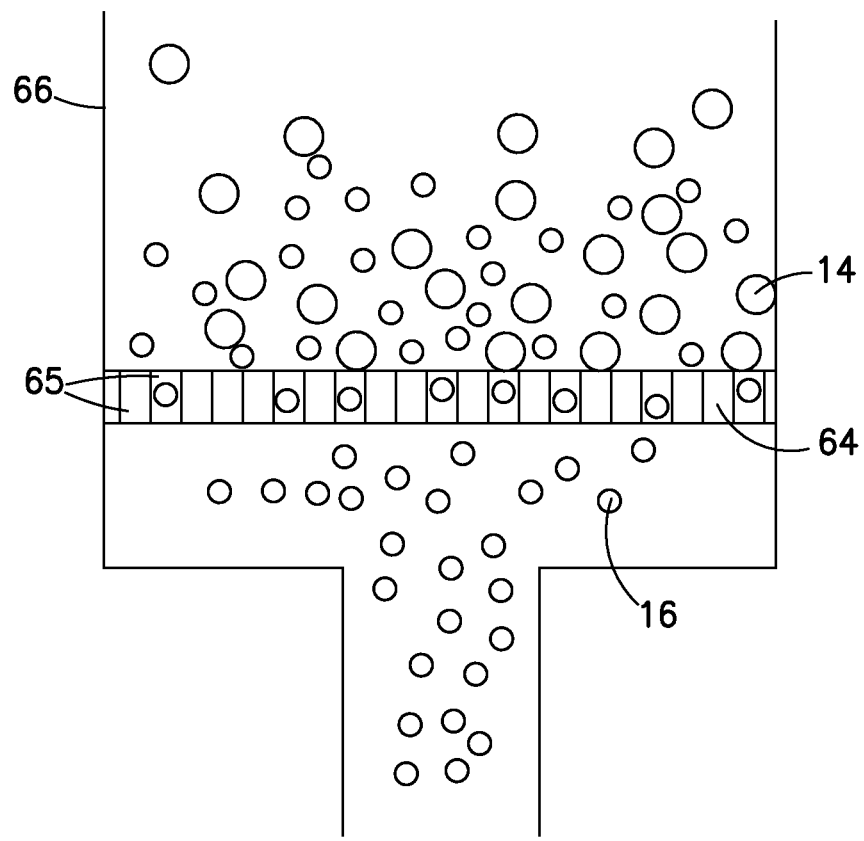
FIG. 9 is a schematic representation of a separation member of a biological fluid collection device in accordance with an embodiment of the present invention.

As stated above and with particular reference to FIGS. 4, 8, and 9, the inlet port 32 is adapted to receive a multi-component blood sample 12 having a first portion, which can be a cellular portion 14, and a second portion, which can be a plasma portion 16. As shown in FIGS. 6 and 9, the filter 64 is adapted to trap the cellular portion 14 within the collection chamber 62 and allow the plasma portion 16 to pass through the filter 64 and into the plasma chamber 66. According to one embodiment, the filter 64, such as a lateral flow filter, includes a plurality of apertures 65 sized to allow the smaller plasma particles of the plasma portion 16 to pass therethrough and into the plasma chamber 66 while trapping the larger cellular particles of the cellular portion 14 in the collection chamber 62 to separate the multi-component blood sample 12.

In one embodiment, the filter 64 may be either hollow fiber membrane filters commercially available, or flat membrane filters, such as track-etch filters commercially available. Membrane filter pore size and porosity can be chosen to optimize separation of clean (i.e., red blood cell free, white blood cell free, and platelet free) plasma in an efficient manner. In another embodiment, the filter 64 includes a lateral flow membrane or lateral flow filter. In other embodiments, the filter 64 may comprise any filter that is able to trap the cellular portion 14 of the blood sample 12 within the collection chamber 62 and allow the plasma portion 16 of the blood sample 12 to pass through the filter 64 to the plasma chamber 66.

Referring back to FIGS. 1-3 and 5, the blood collection device 10 includes an actuation member, which can be in the form of a plunger 36, in communication with the inlet port 32. The actuation member or plunger 36 is transitionable from an initial position in which a portion of the actuation member or plunger is disposed within the housing 30 in an initial position, to an activated position in which the same portion of the actuation member or plunger 36 is displaced from the initial position within the housing 30 and the multi-component blood sample 12 is drawn into the first flow channel 56 of the housing 30 through the inlet port 32.

With continuing reference to FIG. 5, the blood collection device 10 can include a drive element 70 in communication with the inlet port 32. The drive element 70 is powered by power button 71 and is adapted to assist the flow of the multi-component blood sample 12 within the inlet port 32. According to one embodiment, the drive element can be a piezo-electric acoustic drive element.

As shown in FIGS. 4 and 5, the first flow channel 56 can include at least one of a sample stabilizer or a preservative 18. As stated above, this sample stabilizer or preservative 18 can include any one or more of an anticoagulant or a substance well known in the art that can be used to preserve a specific element within a blood sample, such as RNA, a protein analyte, and the like. The first flow channel 56 can also include one or more mixing chambers 74 that include at least one agitation member 72. The agitation member 72 can assist in folding of the sample or lamellation or other flow pattern induced mixing. According to one embodiment, the at least one agitation member 72 can be in the form a flute or rib that is co-molded with the first flow channel 56 to form the mixing chamber 74 and the sample stabilizer or preservative 18 can be coated on the flutes and/or on an inner sidewall surface 57 of the inlet port 32 and/or the first flow channel 56. In operation, the inlet port 32 is adapted to receive the multi-component blood sample 12 and the valve 60 is transitionable from the closed position to the open position subsequent to mixing of the multi-component blood sample 12 with at least one of the sample stabilizer or preservative 18 located within the first flow channel 56.

With reference to FIGS. 6-8, the outlet port 40 is in communication with the plasma chamber 66. The outlet port 40 is also adapted for connection to a point-of-care testing device 22 for closed transfer of a portion of the plasma portion 16 from the plasma chamber 66 to the point-of-care testing device 22. The point-of-care testing device 22 includes a receiving port 24 adapted to receive the outlet port 40 of the blood collection device 10. The testing device 22 is adapted to receive the outlet port 40 of the blood collection device 10 for closed transfer of a portion of the plasma portion 16 (FIG. 8) from the plasma chamber 66 of the outlet port 40 of the blood collection device 10 to the testing device 22. The testing device 22 is adapted to receive the plasma portion 16 to analyze the sample and obtain test results.

To avoid damaging the cells of the specimen as it is collected, a pressure regulator 80, such as a damper pressure regulator, can be provided integrally with the blood collection device 10. This pressure regulator 80 can be in fluid communication with at least one of the inlet port 32, the first flow channel 56, the valve 60, the second flow channel 58, the collection chamber 62, the plasma chamber 66, the filter 64, and/or the outlet port 40.

FIG. 8 illustrates a cross-sectional view of an exemplary embodiment of the outlet port/dispenser 40 in cooperation with the point-of-care testing device 22 for supplying the plasma portion 16 to analyze the blood sample and obtain test results. The outlet port/dispenser 40 can be in the form of a septum that includes flexible members 76, which, when placed in contact with the receiving port 24 of the point of care device 22 and a downward force or a distally directed force D is applied thereto, the flexible members 76 open up to dispense the plasma portion 16. In certain other configurations, the outlet port/dispenser 40 could be utilized to transfer a stabilized whole blood sample or cellular sample for analysis.

With continuing reference to FIGS. 3 and 7, in operation, the blood collection device 10 is connected to an appropriate blood collection set 100 or other line. The clinician pulls the plunger 36 in a proximal direction P to draw in a specimen, such as a multi-component blood sample 12. As stated above, to avoid damaging the cells of the specimen as it is collected, a pressure regulator 80 is provided integrally with the blood collection device 10. As blood is pulled into the inlet port 32, the first flow channel 56, which is coated with a sample stabilizer/preservative 18, includes molded flutes 72 to ensure that good mixing is occurring as the sample is drawn into the inlet port 32. A rotating valve 60 that diverts the sample 12 during a draw of the sample 12 is provided integrally with the housing 30. As the sample 12 is collected, the acoustic driver 70 can be activated which helps move the sample 12 through the first flow channel 56 and the housing 30 of the blood collection device 10 and continues to mix. Once the sample 12 is collected, the clinician disconnects the blood collection device 10 from the collection source and rotates the rotating valve 60 ninety degrees. This rotation of the rotating valve 60, diverts the sample 12 to the second flow channel 58 having a collection chamber 62 and over a filter 64, such as a lateral flow filter as shown in FIG. 9, which separates the cellular portion 14 from the plasma portion 16. A plasma chamber 66 then holds the plasma portion until it is transferred.

To transfer the collected plasma from the blood collection device 10, the clinician places the dispensing port 40 over a receiving port or well 24 of the point-of-care testing device 22. The clinician then advances the plunger 36 in the distal direction D to express the collected plasma into the port or well 24 of the point-of-care testing device 22. The dispensing port 40 has flexible members or posts 76 that flex when depressed and release the plasma portion 16.

Some of the advantages of the blood collection device and the blood separation and testing system of the present disclosure over prior systems are that it is a closed system which reduces blood sample exposure, it provides automatic and fast mixing of the blood sample with an anticoagulant, it facilitates separation of the blood sample without transferring the blood sample to a separate device, and it is capable of transferring pure plasma to a point-of-care testing device. The blood collection device of the present disclosure enables integrated blood collection and plasma creation in a closed system without centrifugation. The clinician may collect and separate the blood sample and then immediately transfer the plasma portion to the point-of-care testing device without further manipulation. This enables collection and transfer of plasma to the point-of-care testing device without exposure to blood. In addition, the blood collection device of the present disclosure minimizes process time by processing the blood within the blood collection device and without external machinery. Further, it eliminates the waste associated with blood collection and plasma separation for an evacuated tube for tests which only require small amounts of blood.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. A biological fluid collection device for a multi-component blood sample, comprising:
    a housing having an inlet port, an outlet port, a first flow channel defined within the housing and in fluid communication with the inlet port, and a second flow channel defined within the housing and in fluid communication with the outlet port;
    a valve disposed between the first flow channel and the second flow channel and transitionable between a closed position and an open position, wherein with the valve in the closed position, the first flow channel is in fluid isolation from the second flow channel, and wherein with the valve in the open position, the first flow channel is in fluid communication with the second flow channel; and
    an actuation member in communication with the inlet port and transitionable from an initial position in which a portion of the actuation member is disposed within the housing in a first position, to an activated position in which the same portion of the actuation member is displaced from the first position within the housing, the actuation member being provided on an opposing end of the housing from the inlet port,
    wherein the second flow channel comprises a collection chamber having a separation member disposed therein and a blood component chamber in communication with the separation member.

2. The biological fluid collection device of claim 1, wherein the inlet port receives the multi-component blood sample.

3. The biological fluid collection device of claim 2, wherein the multi-component blood sample comprises a cellular portion and a plasma portion.

4. The biological fluid collection device of claim 3, wherein the separation member allows the plasma portion to pass through the separation member and into the blood component chamber.

5. The biological fluid collection device of claim 1, wherein the separation member is a lateral flow filter.

6. The biological fluid collection device of claim 2, wherein, with the actuation member in the activated position, the multi-component blood sample is drawn into the first flow channel of the housing through the inlet port.

7. The biological fluid collection device of claim 6, wherein the actuation member comprises a plunger.

8. The biological fluid collection device of claim 2, further comprising a drive element in communication with the inlet port, the drive element adapted to assist the flow of the multi-component blood sample within the inlet port.

9. The biological fluid collection device of claim 8, wherein the drive element comprises an acoustic driver.

10. The biological fluid collection device of claim 1, wherein the first flow channel comprises a sample stabilizer.

11. The biological fluid collection device of claim 1, wherein the first flow channel includes at least one agitation member.

12. The biological fluid collection device of claim 1, wherein the first flow channel includes at least one agitation flute therein and wherein the at least one agitation flute has at least one sample stabilizer coated thereon.

13. The biological fluid collection device of claim 1, wherein the first flow channel comprises a sample stabilizer, and wherein the inlet port receives the multi-component blood sample and the valve is transitionable from the closed position to the open position subsequent to mixing of the multi-component blood sample within the first flow channel.

14. The biological fluid collection device of claim 1, wherein the outlet port is in communication with the blood component chamber.

15. The biological fluid collection device of claim 1, wherein the inlet port receives the multi-component blood sample having a cellular portion and a plasma portion, and wherein the outlet port is connectable to a point-of-care testing device for closed transfer of at least a portion of the plasma portion from the blood component chamber to the point-of-care testing device.

16. The biological fluid collection device of claim 1, wherein the valve comprises a rotatable stop-cock.

17. The biological fluid collection device of claim 1, wherein the actuation member is integral to the biological fluid collection device.

18. The biological fluid collection device of claim 1, wherein the housing includes a first end, a second end, and a side portion, the first end opposite the second end,
    wherein the inlet port extends from the first end,
    wherein the actuation member extends from the second end, and
    wherein the outlet port extends from the side portion in a direction substantially perpendicular to the first end and the second end.

19. A multi-component biological fluid sample separation and testing system, comprising:
    a biological fluid collection and separation device comprising:

a housing having an inlet port, an outlet port, a first flow channel defined within the housing and in fluid communication with the inlet port, and a second flow channel defined within the housing and in fluid communication with the outlet port, the inlet port receives a multi-component blood sample;

a valve disposed between the first flow channel and the second flow channel and transitionable between a closed position and an open position, wherein with the valve in the closed position, the first flow channel is in fluid isolation from the second flow channel, and wherein with the valve in the open position, the first flow channel is in fluid communication with the second flow channel; and an actuation member in communication with the inlet port and transitionable from an initial position in which a portion of the actuation member is disposed within the housing in a first position, to an activated position in which the same portion of the actuation member is displaced from the first position within the housing, the actuation member being provided on an opposing end of the housing from the inlet port, wherein the second flow channel comprises a collection chamber having a separation member disposed therein and a blood component chamber in communication with the separation member; and a testing device having a receiving port connectable to the outlet port of the biological fluid collection and separation device for closed transfer of a portion of the multi-component blood sample from the blood component chamber to the testing device.

20. The multi-component biological fluid sample separation and testing system of claim 19, wherein the testing device comprises a point-of-care testing device.

21. The multi-component biological fluid sample separation and testing system of claim 19, wherein the multi-component blood sample includes a cellular portion and a plasma portion.

22. The multi-component biological fluid sample separation and testing system of claim 21, wherein the separation member allows the plasma portion to pass through the separation member and into the blood component chamber.

23. The multi-component biological fluid sample separation and testing system of claim 19, wherein the separation member is a lateral flow filter.

24. The multi-component biological fluid sample separation and testing system of claim 19, wherein the first flow channel includes at least one sample stabilizer.

25. The multi-component biological fluid sample separation and testing system of claim 19, wherein the first flow channel includes at least one agitation member located therein.

26. The multi-component biological fluid sample separation and testing system of claim 19, wherein the actuation member is integral to the biological fluid collection and separation device.

27. The multi-component biological fluid sample separation and testing system of claim 19, wherein the housing includes a first end, a second end, and a side portion, the first end opposite the second end,
- wherein the inlet port extends from the first end,
- wherein the actuation member extends from the second end, and
- wherein the outlet port extends from the side portion in a direction substantially perpendicular to the first end and the second end.

* * * * *